United States Patent
Wang et al.

(10) Patent No.: US 7,417,110 B2
(45) Date of Patent: Aug. 26, 2008

(54) BIODEGRADABLE POLYPHOSPHORAMIDATES FOR CONTROLLED RELEASE OF BIOACTIVE SUBSTANCES

(76) Inventors: Jun Wang, 720 Rutland Ave., 729 Rose Bldg., Baltimore, MD (US) 21205; Hai-Quan Mao, Block 60 West coast Crescent, #04-01 West Bay Condominium, Singapore, 128040 (SG); Kam Weng Leong, 10242 Breconshire Rd., Ellicott City, MD (US) 21042

(*) Notice: Subject to any disclaimer, the term of this patent is extended or adjusted under 35 U.S.C. 154(b) by 0 days.

(21) Appl. No.: 10/500,565

(22) PCT Filed: May 14, 2002

(86) PCT No.: PCT/SG02/00091

§ 371 (c)(1),
(2), (4) Date: Jan. 7, 2005

(87) PCT Pub. No.: WO03/000776

PCT Pub. Date: Jan. 3, 2003

(65) Prior Publication Data

US 2005/0119450 A1    Jun. 2, 2005

Related U.S. Application Data

(60) Provisional application No. 60/290,833, filed on May 14, 2001.

(51) Int. Cl.
*C08G 79/02* (2006.01)
*C08G 79/04* (2006.01)
*C08J 3/07* (2006.01)

(52) U.S. Cl. .......... 528/398; 528/399; 528/422; 528/425; 524/501; 524/708; 524/710; 424/1.77; 424/457

(58) Field of Classification Search ............... 528/398, 528/399, 422, 425; 524/501, 708, 710; 424/1.77, 424/457
See application file for complete search history.

(56) References Cited

U.S. PATENT DOCUMENTS 5,194,581 A * 3/1993 Leong .................. 528/398

OTHER PUBLICATIONS

HCA 78:30806.*
HCA 107:116051.*

* cited by examiner

*Primary Examiner*—Duc Truong
(74) *Attorney, Agent, or Firm*—Greenberg Traurig (57) ABSTRACT

The present invention is directed to a series of new polycationic biodegradable polyphosphoramidates. Process for making the polymers, compositions containing these polymers and bioactive ligands to enhance the cellular uptake ad intracellular trafficking, articles and methods for delivery of drugs and genes using these polymers are described. A gene delivery system based on these polymers is prepared by complex coacervation of nucleic acid (DNA or RNA) with polymers. Targeting ligands and molecules that could facilitate gene transfer can be conjugated to polymers to achieve selective and enhanced gene delivery. The current invention also provides a complex composition with buffering capacity.

11 Claims, 5 Drawing Sheets

Polymeric Carriers

Figure 9

BIODEGRADABLE POLYPHOSPHORAMIDATES FOR CONTROLLED RELEASE OF BIOACTIVE SUBSTANCES

This application claims the benefit of U.S. Provisional Application Ser. No. 60/290,833 filed May 14, 2001, the teachings of which are incorporated herein by reference.

BACKGROUND OF THE INVENTION

1. Field of the Invention

The present invention generally relates to biodegradable polymer compositions, in particular those containing both phosphoester linkages in the polymer backbone and chargeable groups linked to the backbone through a P—N bond. The polymers of the invention are useful for drug and gene delivery, particularly as carriers for gene therapy and for the delivery of protein drugs.

2. Background

Gene therapy has been progressively developed with the hope that it will be an integral part of medical modalities in the future. Gene delivery system is one of the key components in gene medicine, which directs the gene expression plasmids to the specific locations within the body. The control of gene expression is achieved by influencing the distribution and stability of plasmids in vivo and the access of the plasmids to the target cells, and affecting the intracellular trafficking steps of the plasmids (Mahato, et al., 1999, *Pharmaceutical perspectives of nonviral gene therapy, Adv. Genet.* 41: 95-156). An ideal gene delivery carrier should be bioabsorable, non-toxic, non-immunogenic, stable during storage and after administration, able to access target cells, and efficient in aiding gene expression. As many studies demonstrated, the limitations of viral vectors make synthetic vectors an attractive alternative. Advantages of non-viral vectors include non-immunogenicity, low acute toxicity, versatility, reproducibility and feasibility to be produced on a large scale. Cationic liposome and cationic polymers are the two major types of non-viral gene delivery carriers. Cationic lipids self assemble into organized structures include micelles, plannar bilayer sheets, and lamellar vesicles. Through the condensation process, liposomes and cationic polymers form complexes with DNA due to charge interaction. A large variety of liposomal compositions have been developed for gene delivery (Chesnoy and Huang, 2000. *Structure and function of lipid-DNA complexes for gene delivery, Annu. Rev. Biophys. Biomol. Struct.* 29: 27-47). An effective liposome vector generally composed of a positively charged lipid (e.g. cationic derivatives of cholesterol and diacyl glycerol, quaternary ammonium detergents, lipid derivatives of polyamines, etc.) and a neutral helper lipid (e.g. dioleoyl phosphatidylethanolamine (DOPE) or dioleoyl phosphotidylcholine (DOPC)). Despite early excitement, there are serious limitations to most cationic lipid systems. Several observations have suggested that liposomal systems are relatively unstable after the administration. Significant toxicity upon repeated use has been shown to be associated to liposomal vectors, especially the fusogenic phospholipid (neutral lipid), include the down regulation of PKC dependent immunomodulator synthesis, macrophage toxicity, neurotoxicity and acute pulmonary inflammation (Filion and Phillips, 1998, *Major limitations in the use of cationic liposomes for DNA delivery, Int. J. Pharm.* 162: 159-170).

Because of the limitations of viral vectors, cationic lipids, cationic polymers as the basis of gene delivery systems have gained increasing attention recently. A number of polycations have been reported to effect transfection of DNA, including poly-L-lysine, poly-L-ornithine, poly(4-hydroxy-L-proline ester), polyiminocarbonate containing cyclodextrin, poly[α-(4-aminobutyl)-L-glycolic acid], polyamidoamines, polyamidoamine dendrimers, chitosan, polyethylenimine, poly(2-dimethylaminoethyl methacrylate), etc. Significant progress has been made in the development of polymer based systems, especially biodegradable polymers that have lower toxicity and can mediate gene transfection via condensing DNA into small particles and protecting DNA from enzymatic degradation. Nevertheless, searching for a safer and more efficient gene carrier still remains a major challenge in the field of non-viral gene delivery.

SUMMARY OF THEM INVENTION

The invention provides positively chargeable biodegradable polymers that comprises at least one phosphoester linkage in the polymer backbone and at least one positively chargeable group wherein the positively chargeable group is a substitutent of a side chain attached to the polymer backbone through a phosphoramidate linkage, e.g., a P—N bond.

The invention further provides positively chargeable biodegradable polymer compositions comprising:
  (a) at least one biologically active substance; and
  (b) A positively chargeable biodegradable polymer comprising at least one phosphoester linkage in the polymer backbone and at least one positively chargeable group wherein the positively chargeable group is a substituent of a side chain attached to the polymer backbone through a phosphoramidate linkage.

The invention additionally provides a method of preparing a positively chargeable biodegradable polymers. The method comprising the steps of:

polymerizing at least two monomers to form a polymer with at least one phosphoester linkage in the polymer backbone;

reacting the polymer with a primary or secondary amine having a positively chargeable group or a substituent that can be functionalized to a positively chargeable group under conditions conducive to the formation of a positively chargeable biodegradable polymer comprising at least one phosphoester linkage in the polymer backbone and at least one positively chargeable group wherein the positively chargeable group is a substitutent of a side chain attached to the polymer backbone through a phosphoramidate linkage.

The invention provides a method of preparing a positively chargeable biodegradable polymer composition. The method comprises the steps of:

providing a positively chargeable biodegradable polymer comprising at least one phosphoester linkage in the polymer backbone and at least one positively chargeable group wherein the positively chargeable group is a substitutent of a side chain attached to the polymer backbone through a phosphoramidate linkage.

contacting the positively chargeable biodegradable polymer with a biologically active substance under conditions conducive to the formation of a complex, e.g., a composition, comprising the positively chargeable biodegradable polymer and the biologically active substance.

The invention also provides for the controlled release of a biologically active substance. The method comprises the steps of:

providing a positively chargeable biodegradable polymer composition comprising:
  (a) at least one biologically active substance; and A positively chargeable biodegradable polymer comprising at least one phosphoester linkage in the polymer backbone and at least one positively chargeable group wherein the positively chargeable group is a substituent of a side chain attached to the polymer backbone through a phosphoramidate linkage;

contacting the composition with a biological fluid, cell or tissue under conditions conducive to the delivery of at least a portion of the biologically active substance to the biological fluid, cell or tissue.

The invention further provides methods for gene transfection using the controlled release methods and the positively chargeable biodegradable polymer composition comprising a DNA sequence, a gene or a gene fragment, to deliver a DNA sequence, a gene or a gene fragment to a specified tissue target in a patient. Gene transfection methods of the invention are suitable for use in treatment of any disease or disorder which is currently treatable by gene therapy or is contemplated as a disease or disorder suitable for treatment by gene therapy in the for future. Gene transfection methods of the invention comprise the steps of providing a positively chargeable biodegradable polymer composition comprising:
  (a) at least one DNA fragment, gene or gene fragment; and
  (b) a positively chargeable biodegradable polymer comprising at least one phosphoester linkage in the polymer backbone and at least one positively chargeable group wherein the positively chargeable group is a substituent of a side chain attached to the polymer backbone through a phosphoramidate linkage;
  contacting the composition with a biological fluid, cell or tissue under conditions conducive to the delivery of at least a portion of the DNA sequence gene or gene fragment to the biological fluid, cell or tissue.

DETAILED DESCRIPTION OF THE INVENTION

This invention discloses a new class of cationic biodegradable polymers containing phosphoester group in the backbone and chargeable groups linked to the backbone through a phosphoramidate linkage, e.g., a P—N bond. The biodegradable polyphosphoramidate of the invention comprise the recurring monomeric units shown in the Formula I:

FORMULA I wherein:

$R_1$ is a divalent organic moiety that is aliphatic, aromatic or heterocyclic;

$R_2$ and $R_3$ are each independently selected from the group consisting of hydrogen, alkyl, aryl, heteroaryl, heteroalicyclic, cycloalkyl, aralkyl or cycloalkylalkyl;

each non-hydrogen occurrence of $R_2$ and $R_3$ is substituted with one or more positively chargeable functional groups (e.g. primary amino group, secondary amino group, tertiary amino group and quaternary amino group, etc.); and n is 5 to 2000.

when $R_1$ is $-(CH_2)_a-$ and one of $R_2$ and $R_3$ is hydrogen, the other of $R_3$ and $R_2$ is selected from the group consisting of hydrogen, aryl, heteroaryl, heteroalicylcic, cycloalkyl, aralkyl, and cycloalkylaklyl, wherein a ranges from 2 to 6.

Particularly preferred polymers according to formula I include polymers of formula II:

FORMULA II wherein:

n, $R_2$ and $R_3$ are as defined in Formula I;

$R_4$ and $R_5$ are independently selected from the group consisting of hydrogen, alkyl, cycloalkyl, alkoxy, aryl, heteroaryl, heteroalicyclic, aralkyl, a steroid derivative; and q is an integer from about 1 to about 5.

Preferred positively chargeable biodegradable polymers of the invention are capable of forming a complex with biologically active substance. Preferred biologically active substances include DNA, RNA, proteins, small molecule therapeutics, and the like.

Other preferred positively chargeable biodegradable polymers of the invention include polymers capable of complexing 20-60% by weight of a biologically active substance such as DNA, RNA, proteins, small molecule therapeutics, and the like.

Furthermore, preferred positively chargeable biodegradable polymers of the invention include polymers having between about 5 and about 2,000 phosphoramidate groups, more preferably between about 10 and about 1500 phosphoramidate groups, and particularly preferred are polymers having between about 20 and 1000 phosphoramidate groups. Also preferred are polymers having a molecular weight of between about 1000 and 500,000, more preferable having a molecular weight of between about 2000 and 200,000, particularly preferable are polymers having a molecular weight of between about 2000 and 100,000.

In additional preferred embodiments, positively chargeable biodegradable polymers of the invention further comprise one or more groups that facilitate intracellular or extracellular delivery of a biologically active substance. Preferred groups for facilitating intracellular delivery of a biologically active substance include a lysosomalytic agent, an amphiphilic peptide, a steroid derivative, and the like.

In preferred embodiments, the biodegradable polyphosphoramidate polymers of the invention, including polymers according to Formula I or Formula II, are biocompatible before and upon degradation.

In preferred embodiments, the biologically active substance is negatively charged Preferred biologically active substances include anionic groups such as phosphate groups, carboxylate groups, sulfate groups and other negatively charged bio-compatible groups.

In another embodiment the invention features a coacervate system useful for the delivery of bioactive macromolecules comprising the biodegradable polymer of Formula I.

In another embodiment, the invention features polymer conjugates comprising polymers of Formula I and bioactive ligands that could facilitate cell uptake and intracellular trafficking steps.

In another embodiment of the invention coacervate systems useful for delivery of nucleic acids (DNA or RNA) and/or protein drugs and comprise the biodegradable polymer of Formula I or the above-described polymer conjugates are described.

In a further embodiment, the invention contemplates a process of making polymeric coacervates for delivery of protein drugs or nucleic acid.

This invention also describes a number of procedures for preparing the biodegradable polymers described above.

The biodegradable polymers could be copolymers having one or several different monomeric recurring units described in Formula I.

A lipophilic moiety, e.g. a group bearing cholesterol structural or lipid, could be conjugated to the carriers to enhance the interaction between complexes and cell membrane therefore facilitates cell uptake.

An endolysosomalytic agent, e.g. an amphiphilic peptide, could be conjugated to the carriers to enhance the endosomal escape after cell uptake step.

A nucleus localization signal could be conjugated to the carriers to facilitate the nucleus translocation.

It is a discovery of the present invention that nucleic acid molecules of various chain lengths can complex with these biodegradable polymers of Formula I in aqueous conditions to form coacervates or solid microparticles ranging from submicron to microns in size. These coacervates containing nucleic acids, when appropriately targeted, can transfect cells with phagocytic activity.

According to the present invention, other molecules, especially those carry charges and have relatively higher molecular weights could also be incorporated into the complexes/coacervates.

In a further embodiment, the invention contemplates a process of making polymeric coacervates for delivery of bioactive macromolecules.

In yet another embodiments the invention comprises articles comprising one or several different polymers with structures shown in Formula I and bioactive substances, e.g. nucleic acids and other negatively charged macromolecules for sustained release of these bioactive substances in-vivo and/or in-vitro. Additionally, the bioactive substances can be released in a controlled, sustained manner either an intracellular and extracellular manner.

In a still further embodiment, the invention contemplates a process for preparing biodegradable polyphosphoramidates, which comprises a step of reacting a polymer shown in Formula III, wherein X is a halogen and $R^1$ is as defined in Formula I, with a primary or secondary amine having a general structure as $R^2R_3NH$, wherein $R_2$ and $R_3$ are each independently selected from the group consisting of hydrogen, alkyl, aryl, heteroaryl, heteroalicyclic, cycloalkyl, aralkyl or cycloalkylalkyl wherein each non-hydrogen occurrence of $R_2$ and $R_3$ is substituted with one or more positively chargeable functional groups (e.g. primary amino group, secondary amino group, tertiary amino group and quaternary amino group, etc.).

FORMULA III

In specific, embodiments, one or more charged groups that are present in $R_2$ or $R_3$ are capable of reacting with a P-halogen bond. Preferably, such reactive positively chargeable groups are protected using standard organic chemistry protecting group techniques to prevent reaction of such groups with the P—X bond. The protected primary or secondary amine, $R_2R_3NH$, is then reacted with the polymer of Formula III where X is a halogen. In particular preferred embodiments, reactive positively chargeable groups include primary or secondary amine groups which are protected using standard amine protection methodologies.

In other preferred embodiments, phosphoramidate polymers of the invention can be prepared by formation of a P—N linkage by reacting a polymer of Formula II wherein X is hydrogen with a primary or secondary amine in a polar aprotic solvent mixture such as $DMF/CCl_4$ to Scheme 1.

Scheme 1.

The biodegradable polymeric system described in the present invention achieves sustained and localized delivery of one or more therapeutic agents to a designated biological tissue or site in a patient. In particular, the polymeric system of the invention achieve sustained and localized delivery of one or more genes in skeletal muscles or intradermally and achieve a higher gene transfer efficiencies than other plasmid delivery systems currently under investigation. The biodegradable polymeric carriers described in the present invention achieve gene transfer efficiencies in vitro and in vivo that are superior to other polycationic carriers currently under investigation.

The polyphosphoramidate carriers of the present invention typically offer the following advantages over other biodegradable carriers described in the literatures and patents.

Polyphosphoramidate polymers of the invention are biodegradable wherein the polymers have a cleavable backbone, either hydrolytically or enzymatically. The two most effective polymeric carriers currently available, PEI and various dendrimeric materials, are not biodegradable and their fate, in vivo, after administration is still unclear.

Polyphosphoramidate polymers of the invention are biocompatible before, during and after biodegradation. Biodegradation breakdown products are typically non-toxic. The polyphosphoramidate polymers of the invention are less cytotoxic than poly-L-lysine, PEI and liposome compositions in vitro. In a preferred embodiment, polymers of Formula I are degraded to phosphate, 1,2-propanediol and amines $R^2R^3NH$. By prudent selection of the side chains, the polymer potentially has minimal toxicity before and upon degradation.

Polyphosphoramidate polymers described in the present patent have higher molecule weight than most other biodegradable carriers reported in the literatures whose number average molecular weights are in the range of 3,000 to 9,000. The biodegradable polymers described here generally have number average molecular weights in the range of 10,000 to 500,000. Higher molecular weight of the polymeric carriers generally increases the binding capacity of the carriers such that the polymers of the invention typically exhibit superior uptake of DNA and protein.

The structures of polyphosphoramidate polymers are tailorable to have variable charged groups with different pKb, different charge density, molecular weight, hydrophilicity/hydrophobicity balance to optimize the transfection activity of the carriers. An endolysosomalytic agent, e.g. an amphiphilic peptide, may be conjugated to the carriers to enhance the endosomal escape after cell uptake step. A lipophilic moiety, e.g. a group bearing cholesterol structural or lipid, may be conjugated to the carriers to enhance the interaction between complexes and cell membrane therefore facilitate cell uptake. A nucleus localization signal could be conjugated to the carriers to facilitate the nucleus translocation.

Polyphosphoramidates suitable for use in the invention may be modified to comprise one or more specific ligands conjugated to the side chain or as a side chain group to enhance the cellular uptake of one or more bioactive molecules (nucleic acids and proteins) dispersed in carrier polymer and/or achieve tissue/cell specific delivery of the bioactive cargo.

Polyphosphoramidate polymers suitable for use in the methods of the invention typically posses higher molecular weights than polymeric carriers disclosed in the art such that complexes/coacervates comprising the polyphosphoramidates of the invention are more stable than other polycationic materials with lower molecular weights.

Polyphosphoramidate polymers and compositions comprising at least one bioactive molecule and a polyphosphoramidate polymer are prepared by reproducible and easily scalable procedures.

An attractive coacervate delivery system requires a delicate balance among factors such as the simplicity of preparation, cost effectiveness, nucleic acids loading level, controlled release ability, storage stability, and immunogenicity of the components. The gene delivery system described here may offer advantages compared to other particulate delivery systems, including the liposomal system. The problems of instability, low loading level, and controlled release ability are better resolved with these polymeric systems. Compared to other synthetic polymeric systems, such as the extensively studied polylactic/polyglycolic copolymers, the mild conditions of coacervate formulation are appealing. Unlike the solvent evaporation and hot-melt techniques used to formulate synthetic polymeric coacervates, complex coacervation requires neither contact with organic solvents nor heat. It is also particularly suitable for encapsulating bio-macromolecules such as nucleic acids and proteins not only through passive solvent capturing but also by direct charge-charge interactions.

Targeting ligands can be directly bound to the surface of the coacervates. Alternatively, such ligands can be conjugated to the polymeric carriers to form molecular conjugates, which then complex with nucleic acids and/or proteins. Targeting ligands according to the present invention are any molecules, which bind to specific types of cells in the body. These may be any types of molecules for which a cellular receptor exists. Preferably the cellular receptors are expressed on specific cell types only. Examples of targeting ligands that may be used are hormones, antibodies, cell-adhesion molecules, oligosaccharides, drugs, and neurotransmitters.

The method of the present invention involves a coacervation process described in U.S. Pat. No. 5,972,707 (Roy, et al., 1999, Gene Delivery System) and U.S. Pat. No. 6,025,337 (Truong, et al., 2000, Solid Microparticles for Gene Delivery). The process is optimized in this invention to best suit the complexation of nucleic acids and biodegradable carriers of Formula I.

It is a discovery of the present invention that different polymers with different charged groups, e.g. different amino groups with a wide range of acidity (pKb), could be included into one coacervate/complex system for the intracellular delivery. Such a system could offer buffering capacity similar to that of PEI.

Polyphosphoramidates suitable for use in the methods of the present invention include any and all different single pure isomers and mixtures of two or more isomers. The term isomer is intended to include diastereoisomers, enantiomers, regioisomers, structural isomers, rotational isomers, tautomers, and the like. For compounds which contain one or more stereogenic centers, e.g., chiral compounds, the methods of the invention may be carried out with a enantiomerically enriched compound, a racemate, or a mixture of diastereomers. Preferred enantiomerically enriched compounds have an enantiomeric excess of 50% or more, more preferably the compound has an enantiomeric excess of 60%, 70%, 80%, 90%, 95%, 98%, or 99% or more.

Polyphosphoramidates suitable for use in the methods of the present invention include any and all molecular weight distribution profiles, i.e., polymers having a $M_w$, or $M_n$ of between 1 and about 50, more typically a $M_w$, or $M_n$ between about 1.2 and about 10. Moreover, polyphosphroamidates of the invention have a polydispersity index of between about 1 and about 5.

As also discussed above, typical subjects for administration in accordance with the invention are mammals, such as primates, especially humans.

Biodegradable polymers differ from non-biodegradable polymers in that they can be degraded during in vivo therapy. This generally involves breaking down the polymer into its monomeric subunits. In principle, the ultimate hydrolytic breakdown products of polymers suitable for use in the methods of the present invention should be biocompatible, non-toxic and easily excreted from a patient's body. However, the intermediate oligomeric products of the hydrolysis may have different properties. Thus, toxicology of a biodegradable polymer intended for implantation or injection, even one synthesized from apparently innocuous monomeric structures, is typically determined after one or more toxicity analyses.

The biodegradable polymer of the invention is preferably sufficiently pure to be biocompatible itself and remains biocompatible upon biodegradation. "Biocompatible" is defined to mean that the biodegradation products and/or the polymer itself are nontoxic and result in only minimal tissue irritation when instilled in the bladder or transported or otherwise localized to other tissues within a patient.

It will be appreciated that the actual preferred amounts of therapeutic agent or other component used in a given composition will vary according to the therapeutic agent being utilized including the polymer system being employed, the mode of application, the particular site of administration, etc. Optimal administration rates for a given protocol of administration can be readily ascertained by those skilled in the art using conventional dosage determination tests conducted with regard to the foregoing guidelines.

As used herein, "alkyl" is intended to include branched, straight-chain and cyclic saturated aliphatic hydrocarbon groups including alkylene, having the specified number of carbon atoms. Examples of alkyl include, but are not limited to, methyl, ethyl, n-propyl, i-propyl, n-butyl, s-butyl, t-butyl, n-pentyl, and s-pentyl. Alkyl groups typically have 1 to about 16 carbon atoms, more typically 1 to about 20 or 1 to about 12 carbon atoms. Preferred alkyl groups are $C_1$-$C_{20}$ alkyl groups, more preferred are $C_{1-12}$-alkyl and $C_{1-6}$-alkyl groups. Especially preferred alkyl groups are methyl, ethyl, and propyl.

As used herein, "heteroalkyl" is intended to include branched, straight-chain and cyclic saturated aliphatic hydrocarbon groups including alkylene, having the specified number of carbon atoms and at least one heteroatom, e.g., N, O or S. Heteroalkyl groups will typically have between about 1 and about 20 carbon atoms and about 1 to about 8 heteroatoms, preferably about 1 to about 12 carbon atoms and about 1 to about 4 heteroatoms. Preferred heteroalkyl groups include the following groups. Preferred alkylthio groups include those groups leaving one or more thioether linkages and from 1 to about 12 carbon atoms, more preferably from 1 to about 8 carbon atoms, and still more preferably from 1 to about 6 carbon atoms. Alylthio groups having 1, 2, 3, or 4 carbon atoms are particularly preferred. Prefered alkylsulfinyl groups include those groups having one or more sulfoxide (SO) groups and from 1 to about 12 carbon atoms, more preferably from 1 to about 8 carbon atoms, and still more preferably from 1 to about 6 carbon atoms. Alkylsulfinyl groups having 1, 2, 3, or 4 carbon atoms are particularly preferred. Preferred alkylsulfonyl groups include those groups having one or more sulfonyl ($SO_2$) groups and from 1 to about 12 carbon atoms, more preferably from 1 to about 8 carbon atoms, and still more preferably from 1 to about 6 carbon atoms. Alylsulfonyl groups having 1, 2, 3, or 4 carbon atoms are particularly preferred. Preferred aminoalkyl groups include those groups having one or more primary, secondary and/or tertiary amine groups, and from 1 to about 12 carbon atoms, more preferably from 1 to about 8 carbon atoms, and still more preferably from 1 to about 6 carbon atoms. Aminoalkyl groups having 1, 2, 3, or 4 carbon atoms are particularly preferred.

As used herein, "heteroalkenyl" is intended to include branched, straight-chain and cyclic saturated aliphatic hydrocarbon groups including alkenylene, having the specified number of carbon atoms and at least one heteroatom, e.g., N, O or S. Heteroalkenyl groups will typically have between about 1 and about 20 carbon atoms and about 1 to about 8 heteroatoms, preferably about 1 to about 12 carbon atoms and about 1 to about 4 heteroatoms. Preferred heteroalkenyl groups include the following groups. Preferred alkylthio groups include those groups having one or more thioether linkages and from 1 to about 12 carbon atoms, more preferably from 1 to about 8 carbon atoms, and still more preferably from 1 to about 6 carbon atoms. Alkenylthio groups having 1, 2, 3, or 4 carbon atoms are particularly preferred. Prefered alkenylsulfinyl groups include those groups having one or more sulfoxide (SO) groups and from 1 to about 12 carbon atoms, more preferably from 1 to about 8 carbon atoms, and still more preferably from 1 to about 6 carbon atoms. Alkenylsulfinyl groups having 1, 2, 3, or 4 carbon atoms are particularly preferred. Preferred alkenylsulfonyl groups include those groups having one or more sulfonyl ($SO_2$) groups and from 1 to about 12 carbon atoms, more preferably from 1 to about 8 carbon atoms, and still more preferably from 1 to about 6 carbon atoms. Alkenylsulfonyl groups having 1, 2, 3, or 4 carbon atoms are particularly preferred. Preferred aminoalkenyl groups include those groups having one or more primary, secondary and/or tertiary amine groups, and from 1 to about 12 carbon atoms, more preferably from 1 to about 8 carbon atoms, and still more preferably from 1 to about 6 carbon atoms. Aminoalkenyl groups having 1, 2, 3, or 4 carbon atoms are particularly preferred.

As used herein, "heteroalkynyl" is intended to include branched, straight-chain and cyclic saturated aliphatic hydrocarbon groups including alkynylene, having the specified number of carbon atoms and at least one heteroatom, e.g., N, O or S. Heteroalkynyl groups will typically have between about 1 and about 20 carbon atoms and about 1 to about 8 heteroatoms, preferably about 1 to about 12 carbon atoms and about 1 to about 4 heteroatoms. Preferred heteroalkynyl groups include the following groups. Preferred alkynylthio groups include those groups having one or more thioether linkages and from 1 to about 12 carbon atoms, more preferably from 1 to about 8 carbon atoms, and still more preferably from 1 to about 6 carbon atoms. Alkynylthio groups having 1, 2, 3, or 4 carbon atoms are particularly preferred. Preferred alkynylsulfinyl groups include those groups having one or more sulfoxide (SO) groups and from 1 to about 12 carbon atoms, more preferably from 1 to about 8 carbon atoms, and still more preferably from 1 to about 6 carbon atoms. Alkynylsulfinyl groups having 1, 2, 3, or 4 carbon atoms are particularly preferred. Preferred alkynylsulfonyl groups include those groups having one or more sulfonyl ($SO_2$) groups and from 1 to about 12 carbon atoms, more preferably from 1 to about 8 carbon atoms, and still more preferably from 1 to about 6 carbon atoms. Alkynylsulfonyl groups having 1, 2, 3, or 4 carbon atoms are particularly preferred. Preferred aminoalkynyl groups include those groups having one or more primary, secondary and/or tertiary amine groups, and from 1 to about 12 carbon atoms, more preferably from 1 to about 8 carbon atoms, and still more preferably from 1 to about 6 carbon atoms. Aminoalkynyl groups having 1, 2, 3, or 4 carbon atoms are particularly preferred.

As used herein, "cycloalkyl" is intended to include saturated ring groups, having the specified number of carbon atoms, such as cyclopropyl, cyclobutyl, cyclopentyl, or cyclohexyl. Cycloalkyl groups typically will have 3 to about 8 ring members.

In the term "($C_{3-6}$ cycloalkyl)$C_{1-4}$ alkyl", as defined above, the point of attachment is on the alkyl group. This term encompasses, but is not limited to, cyclopropylmethyl, cyclohexylmethyl, cyclohexylmethyl.

As used here, "alkenyl" is intended to include hydrocarbon chains of straight, cyclic or branched configuration, including alkenylene, and one or more unsaturated carbon-carbon bonds which may occur in any stable point along the chain, such as ethenyl and propenyl. Alkenyl groups typically will have 2 to about 12 carbon atoms, more typically 2 to about 12 carbon atoms.

As used herein, "alkynyl" is intended to include hydrocarbon chains of straight, cyclic or branched configuration, including alkynylene, and one or more triple carbon-carbon bonds which may occur in any stable point along the chain, such as ethynyl and propynyl. Alkynyl groups typically will have 2 to about 20 carbon atoms, more typically 2 to about 12 carbon atoms.

As used herein, "haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1). Examples of haloalkyl include, but are not limited to, trifluoromethyl, trichloromethyl, pentafluoroethyl, and pentachloroethyl. Typical haloalkyl groups will have 1 to about 16 carbon atoms, more typically 1 to about 12 carbon atoms.

As used herein, "alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Alkoxy groups typically have 1 to about 16 carbon atoms, more typically 1 to about 12 carbon atoms.

"Prodrugs" are intended to include any covalently bonded carriers which release the active parent drug according to formula I in vivo when such prodrug is administered to a mammalian subject. Prodrugs of a compound are prepared by modifying functional groups present in the drug compound in such a way that the modifications are cleaved, either in routine manipulation or in vivo, to the parent compound.

Combinations of substituents and/or variables are permissible only if such combinations result in stable compounds. A stable compound or stable structure is meant to imply a compound that is sufficiently robust to survive isolation to a useful degree of purity from a reaction mixture, and formulation into an effective therapeutic agent.

As used herein, the term "aliphatic" refers to a linear, branched, cyclic alkane, alkene, or alkyne. Preferred aliphatic groups in the poly(phosphoester-co-amide) polymer of the invention are linear or branched and have from 1 to 20 carbon atoms.

As used herein, the term "aryl" refers to an unsaturated cyclic carbon compound with 4n+2 electrons where n is a non-negative integer, about 5-18 aromatic ring atoms and about 1 to about 3 aromatic rings.

As used herein, the term "heterocyclic" refers to a saturated or unsaturated ring compound having one or more atoms other than carbon in the ring, for example, nitrogen, oxygen or sulfur.

The polymers of the invention are usually characterized by a release rate of the therapeutic agent in vivo that is controlled at least in part as a function of hydrolysis of the phosphoester bond of the polymer during biodegradation. Additionally, the therapeutic agent to be released may be conjugated to the sidechain of the phosphramidate repeat unit to form a pendant drug delivery system. Further, other factors are also important.

The life of a biodegradable polymer in vivo also depends upon its molecular weight, crystallinity, biostability, and the degree of cross-linking. In general, the greater the molecular weight, the higher the degree of crystallinity, and the greater the biostability, the slower biodegradation will be.

The therapeutic agent of the invention can vary widely with the purpose for the composition. The agnet(s) may be described as a single entity or a combination of entities. The delivery system is designed to be used with therapeutic agents having high water-solubility as well as with those having low water-solubility to produce a delivery system that has controlled release rates. The terms "therapeutic agent" and "biologically active substance" include without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

Non-limiting examples of useful therapeutic agents; and biologically active substances include the following expanded therapeutic categories: anabolic agents, antacids, anti-asthmatic agents, anti-cholesterolemic and anti-lipid agents, anti-coagulants, anti-convulsants, anti-diarrheals, anti-emetics, anti-spasmodic agents, anti-inflammatory agents, anti-manic agents, anti-nauseants, anti-neoplastic agents, anti-obesity agents, anti-pyretic and analgesic agents, anti-spasmodic agents, anti-thrombotic agents, anti-uricemic agents, anti-anginal agents, antihistamines, anti-tussives, appetite suppressants, biologicals, cerebral dilators, coronary dilators, decongestants, diuretics, diagnostic agents, erythropoietic agents, expectorants, gastrointestinal sedatives, hyperglycemic agents, hypnotics, hypoglycemic agents, ion exchange resins, laxatives, mineral supplements, mucolytic agents, neuromuscular drugs, peripheral vasodilators, psychotropics, sedatives, stimulants, thyroid and anti-thyroid agents, uterine relaxants, vitamins, antigenic materials, and prodrugs.

Specific examples of useful therapeutic agents and biologically active substances, i.e., bioactive molecules, from the above categories include: (a) anti-neoplastics such as androgen inhibitors, antimetabolites, cytotoxic agents, immunomoldulators; (b) anti-tussives such as dextromethorphan, dextromethorphan hydrobromide, noscapine, carbetapentane citrate, and chlophedianol hydrochloride; (c) antihistamines such as chlorpheniramine maleate, phenindamine tartrate, pyrilamine maleate, doxylamine succinate, and phenyltoloxamine citrate; (d) decongestants such as phenylephrine hydrochloride, phenylpropanolamine hydrochloride, pseudoephedrine hydrochloride, and ephedrine; (e) various alkaloids such as codeine phosphate, codeine sulfate and morphine; (f) mineral supplements such as potassium chloride, zinc chloride, calcium carbonates, magnesium oxide, and other alkali metal and alkaline earth metal salts; (g) ion exchange resins such as cholestryramine; (h) anti-arrhythmics such as N-acctylprocainamide; (i) antipyretics and analgesics such as acetaninophen, aspirin and ibuprofen; (j) appetite suppressants such as phenyl-propanolamine hydrochloride or caffeine; (k) expectorants such as guaifenesin; (l) antacids such as aluminum hydroxide and magnesium hydroxide; (m) biologicals such as peptides, polypeptides, proteins and amino acids, hormones, interferons or cytokines and other bioactive peptidic compounds, such as hGH, tPA, calcitonin, ANF, EPO and insulin; (n) anti-infective agents such as anti-fungals, anti-virals, antiseptics and antibiotics; and (o) antigenic materials, partricularly those useful in vaccine applications.

Preferably, the therapeutic agent or biologically active substance is selected from the group consisting of DNA, polysaccharides, growth factors, hormones, anti-angiogenesis factors, interferons or cytokines, and pro-drugs. In a particularly preferred embodiment, the therapeutic agent is a DNA vaccine comprising a DNA sequence encoding an antigen, a DNA sequence encoding a cytokine or a mixture of DNA sequences encoding an antigen and a cytokine.

The therapeutic agents are used in amounts that are therapeutically effective. While the effective amount of a therapeutic agent will depend on the particular material being used, amounts of the therapeutic agent from about 1% to about 65% have been easily incorporated into the present delivery systems while achieving controlled release. Lesser amounts may be used to achieve efficacious levels of treatment for certain therapeutic agents.

In addition, the polymer composition of the invention can also comprise polymer blends of the polymer of the invention with other biocompatible polymers, so long as they do not interfere undesirably with the biodegradable characteristics of the composition. Blends of the polymer of the invention with such other polymers may offer even greater flexibility in designing the precise release profile desired for targeted drug delivery or the precise rate of biodegradability desired for structural implants such as for orthopedic applications. Examples of such additional biocompatible polymers include other polycarbonates; polyesters; polyorthoesters; polyamides; polyurethanes; poly(iminocarbonates); and polyanhydrides.

As a drug delivery device, the polymer compositions of the invention provide a polymeric matrix capable of sequestering a biologically active substance and provide predictable, controlled delivery of the substance. The polymeric matrix then degrades to non-toxic residues.

It will be understood, however, that the specific dose level for any particular patient will depend upon a variety of factors including the activity of the specific compound employed, the age, body weight, general health, sex, diet, time of administration, route of administration, and rate of excretion, drug combination (i.e., other drugs being administered to the patient), the severity of the particular disease undergoing therapy, and other factors, including the judgment of the prescribing medical practitioner.

A positively chargeable biodegradable polymer composition of the invention also may be packaged together with instructions (i.e. written, such as a written sheet) for treatment of a disorder as disclosed herein, e.g. instruction for treatment of a subject that is susceptible to or suffering from a disease or disorder which may be treated by administration of a bioactive molecule e.g., therapeutic agent, dispersed in the positively chargeable biodegradable polymer composition.

A positively chargeable biodegradable polymer composition of the invention be administered parenterally, preferably in a sterile non-toxic, pyrogen-free medium. The drug, depending on the vehicle and concentration used, can either be suspended or dissolved in the vehicle. Advantageously, adjuvants such as local anesthetics, preservatives and buffering agents can be dissolved in the vehicle. The term parenteral as used herein includes injections and the like, such as subcutaneous, intradermal, intravascular (e.g., intravenous), intramuscular, intrasternal, spinal, intrathecal, and like injection or infusion techniques, with subcutaneous, intramuscular and intravascular injections or infusions being preferred.

A positively chargeable biodegradable polymer composition of the invention also may be packaged together with instructions (i.e. written, such as a written sheet) for treatment of a disorder as disclosed herein, e.g. instruction for treatment of a subject that is susceptible to or suffering from inflammation, cellular injury disorders, or immune system disorders.

The following examples are illustrative of the invention. All documents mentioned herein are incorporated herein by reference.

EXAMPLES

The following examples are of offered by way of illustration and are not intended to limit the invention in any manner.

Example 1

Figure 3:
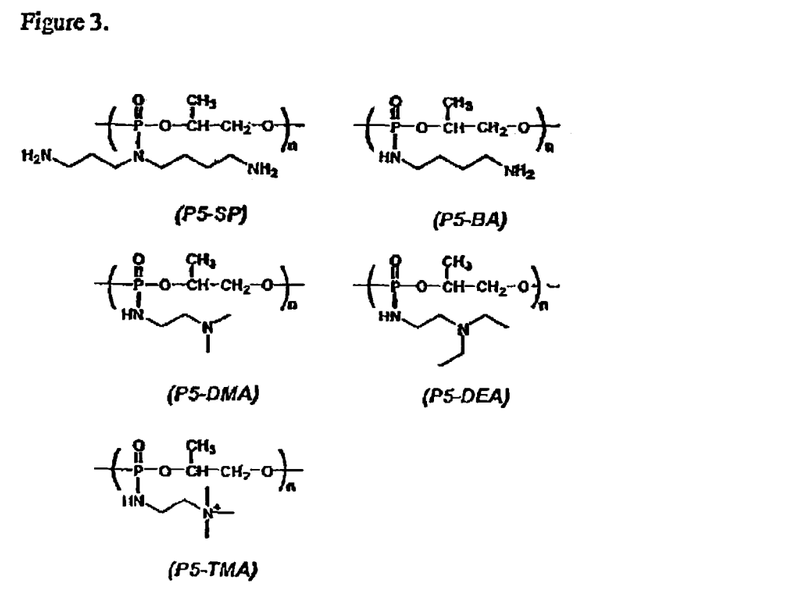
FIG. 3. Structures of P5-SP, P5-BA, P5-DMA, P5-DEA and P5-TMA.

Synthesis and Characterization of Polyphosphoramidates 1.1 Synthesis of P5-SP (Structure Shown in FIG. 3)

Figure 1:
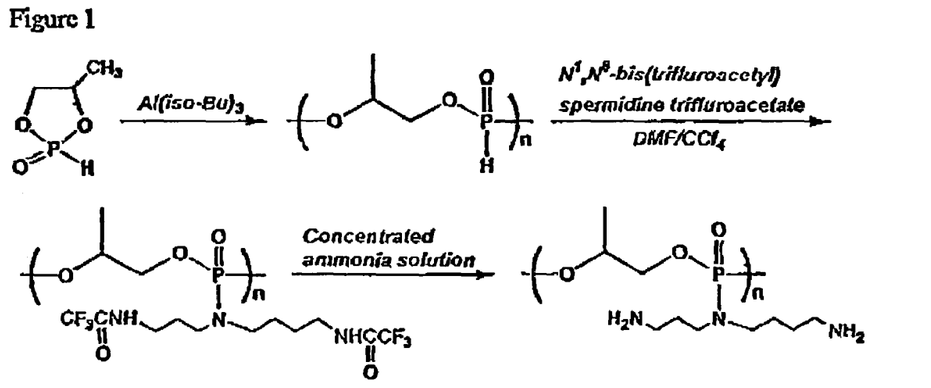
FIG. 1. Synthesis scheme of P5-SP.

The synthetic scheme of P5-SP is shown in FIG. 1. Poly (4methyl-2-oxo-2-hydro-1,3,2-dioxapholane) is synthesized according to the procedure described in the literature (Biela T, Penczek S, and Slomkowski S, 1982, *Racemic and optimal active poly*(4-methyl-2-oxo-2-hydro-1,3,2-dioxapholane): Synthesis and oxidation to the polyacids. Makromol. Chem. Rapid Commun. 3: 667-671). Briefly, 2-hydroxy-4-methyl-1,3,2-dioxapholane (58 g, 0.475 mol) [freshly prepared according to Lucas' method (Lucas H J, Mitchell F W, Jr., and Scully C N, 1950. *Cyclic phosphites of some aliphatic glycols. J. Am. Chem. Soc.* 72: 5491-5497) is polymerized in 200 ml of freshly dried $CHCl_3$ at room temperature for 48 hours. Polymerization is initiated with triisobutylaluminum (1 wt %, 4 ml of 15% solution in heptane). The polymer is obtained by precipitation into anhydrous benzene. This polymer become insoluble in chloroform after precipitation, but it is soluble in anhydrous DMF.

Poly(4-methyl-2-oxo-2-hydro-1,3,2-dioxapholane) (1.094 g, 8.9 mmol P—H groups) is dissolved in anhydrous DMF (10 ml). To this solution is added 5 ml of anhydrous $CCl_4$ and $N^1,N^8$-bis(trifluroacetyl)spermidine trifluroacetate (10.8 mmol, 4.9 g) in 10 ml of DMF using a syringe, followed by addition of 5 ml of anhydrous triethylamine under ice-water bath. The reaction is performed at 0 C for 30 minutes then at room temperature overnight. The resulted solution is concentrated and product is obtained by precipitating in water followed by drying under vacuum.

Figure 2:
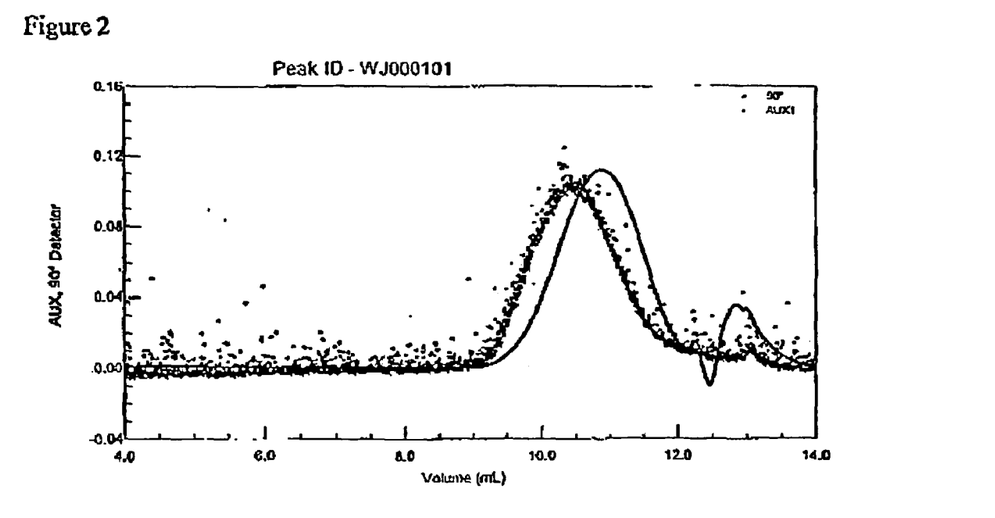
FIG. 2. Gel permeation chromatograph of P5-SP.

The resulted polymer is suspended in 30 ml of concentrated ammonia solution and the mixture is stirred at 60 C for 16 hours. The solution is concentrated and dialyzed against water overnight using a dialysis tubing with a MWCO of 7,500. P5-SP is obtained after lyophilizing the dialyzed solution. The structure of P5-SP is confirmed by proton-NMR: $\delta$(ppm): 1.35-1.4 (d, 3H), 1.5-1.7 (4H), 1.75-1.95 (2H), 2.65-2.95 (4H), 3.0-3.2 (4H), 3.75-4.15 (m, 2H), 4.35-4.65 (d, b, 1H). FIG. 2 shows a typical chromatograph by gel permeation chromatography analysis of P5-SP. It is indicated that P5-SP synthesized has a weight average molecular weight of $4.58 \times 10^4$, and number average molecular weight of $3.14 \times 10^4$ (Polydispersity=1.46).

1.2 Synthesis of P5-DMA (Structure Shown in FIG. 3)

To a solution of poly(4-methyl-2-oxo-2-hydro-1,3,2-dioxapholane) in anhydrous DMF cooled with ice-water bath, was added 5 mL of anhydrous $CCl_4$ and N,N-dimethylethylenediamine (20% excess to P—H) solution in, followed by addition of large excess of triethylamine. The reaction was performed at 0 C for 30 minutes and at room temperature overnight. P5-DMA was obtained by dialysis against water using a dialysis member with a MWCO of 2,000.

To the solution of P5-DMA (100 mg) in 5 ml of methanol was added $CH_3I$ (1 ml) and the mixture was allowed to stay at room temperature overnight. The resulted solution was concentrated and precipitated into ether. P5-TMA was obtained as yellowish power. The number average molecular weight of P5-TMA was $2.62 \times 10^4$ as measured by GPC/LS/RI method.

P5-BA, P5-DEA and P5-TMA (Structures are shown in FIG. 3) are synthesized according to a similar procedure.

Example 2

Assay for the Cytotoxicity of Polyphosphoramidates (PPAs)

Cytotoxicity of polyphosphoramidates (P5-SP, P5-BA, P5-DMA, P5-DEA and P5-TMA) in comparison with other potential gene carriers (poly-L-lysine (PLL) and polyethylenimine (PEI) is evaluated using the WST-1 dye reduction assay. COS-7 cells are seeded in a 96 well plate 24 hours before the assay at the density of $5 \times 10^4$ cells/well The cells are incubated 4 hours with 100 µl of DMEM medium complemented with 10% fetal bovine serum (FBS) containing various PPAs, or PLL or PEI at different concentrations ranging from 0 to 500 µg/ml. The medium in each well is replaced with 100 µl of fresh complete medium and cells are cultured for an additional 20 hrs. Ten microliters of WST-1 reagent (Roche Molecular Biochemicals) is added to each well and allowed reacting for 4 hrs at 37° C. The absorbance of the supernatant at 450 nm (use 655 nm as a reference wavelength) is measured using a microplate reader (Model 550, Bio-Rad Lab. Hercules, Calif.).

Figure 4:
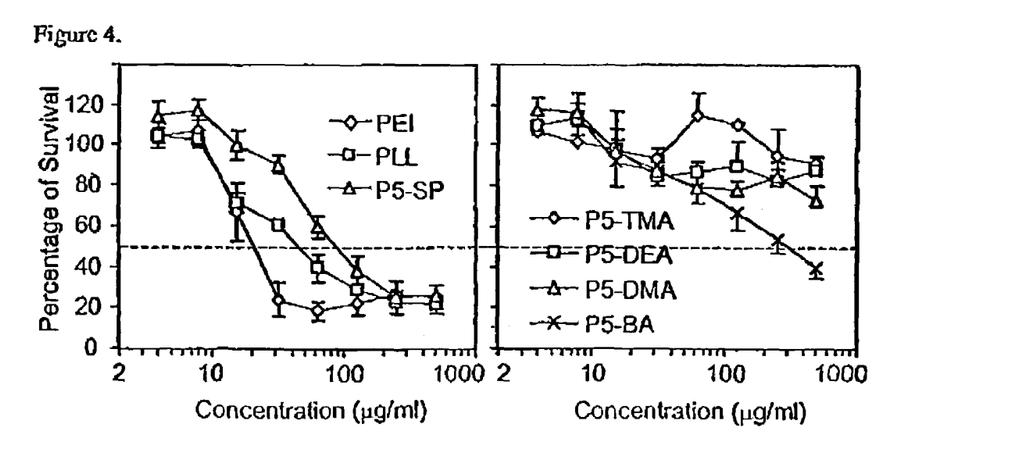
FIG. 4. Cytotoxicity of PPAs in COS-7 Cells as compared with PEI and PLL.

The assay results (FIG. 4) indicate that polyphosphoramidates exhibit lower cytotoxicity in culture than widely used polycationic carrier, PLL and PEI. The $LD_{50}$ of PEI in this assay is 20 µg/ml, $LD_{50}$ of PLL is 42 µg/ml, $LD_{50}$ of P5-SP is 85 µg/ml, $LD_{50}$ of P5-BA is 300 µg/ml, $LD_{50}$ of DMA or DEA or TMA is well beyond 500 µg/ml. It is clear that PPAs have lower cytotoxicity than PLL and PEI. PPAs with tertiary amino group and quaternary amino groups have the lowest cytotoxicity in this assay.

Example 3

Gel Retardation Assay for the DNA Binding Capacity of PPAs

Figure 5:
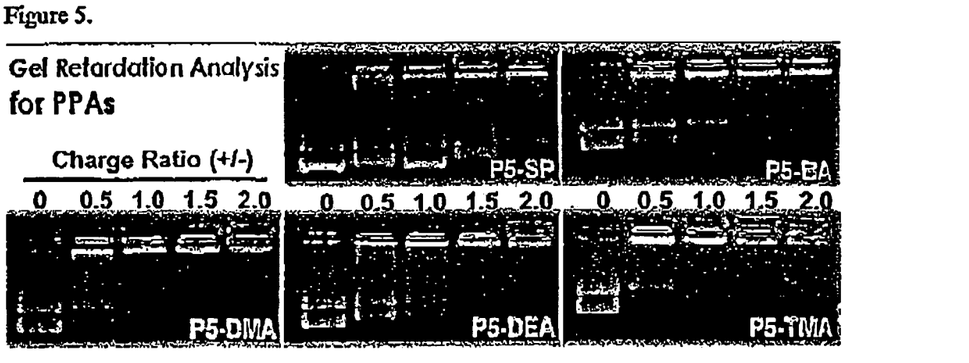
FIG. 5. Gel electrophoretic analysis of the complexation of PPAs with DNA.

The formation of PPA-DNA coacervates is examined be their electrophorectic mobility on an agarose gel at various charge ratios of PPAs to plasmid DNA (FIG. 5). No migration of the plasmid DNA occurred at charge ratio larger than 1.0 (P5-DMA, P5-DEA and P5-TMA) or 1.5 (P5-BA) or 2.0 (P5-SP). This lack of migration is due to neutralization of the nucleic acid by PPAs, suggesting the polycationic nature of PPAs. PPAs with tertiary amino groups and quternary amino groups appear to have higher DNA binding capacity at the same charge ratio.

Example 4

Preparation of PPA-DNA Coacervates and Coacervates with Chloroquine Sulfate

PPA is dissolved in saline at a concentration of 2-10 mg/ml. To this solution is added plasmid DNA dissolved in saline to yield desired N/P ratios, followed by brief vortexing, and the mixture is allowed to stand at room temperature for 30 minutes. The coacervates prepared according to this procedure are used directly for transfection study unless stated otherwise. The efficiency of complexation of DNA is close to 100% when the N/P ratio is over 1.0 as revealed by gel electrophoretic mobility analysis.

Chloroquine sulfate (CQ) has been widely proven to be an effective reagent to disrupt lysosomes and enhance the transfection efficiency in many polycationic gene delivery systems. CQ is co-encapsulated into the coacervates simply by incorporating CQ into the PPA solution and their forming coacervates according to the same procedure. The CQ incorporated coacervates are used for in vitro transfection without further purification since the total amount of CQ added is still within the non-toxic concentration range.

Example 5

Transfection Efficiency of PCEP-DNA Complex in Different Cell Lines

In vitro transfection of HEK 293 cells with PPA-DNA coacervates is evaluated using luciferase as a marker gene. Cells are seeded 24 hours prior to transfection into a 24-well plate (Becton-Dickinson, Lincoln Park, N.J.) at a density of $8 \times 10^4$ per well with 1 ml of complete medium (DMEM containing 10% FBS, supplemented with 2 mM L-glutamate, 50 units/ml penicillin and 50 µg/ml streptomycin). At the time of transfection, the medium in each well is replaced with 1 ml of serum free DMEM. PPA-DNA coacervates or PEI-DNA complexes or PLL-DNA complexes or Transfast™-DNA complexes are incubated with the cells for 3 hours at 37° C. The medium is replaced with 1 ml of fresh complete medium and cells are further incubated for 48 hours. All the transfection tests are performed in triplicate. After the incubation, cells are permeabilized with 200 µl of cell lysis buffer (Promega Co., Madison, Wis.). The luciferase activity in cell extracts is measured using a luciferase assay kit (Promega Co., Madison, Wis.) on a luminometer (Lumat9605, EG&G Wallac). The light units (LU) are normalized against protein concentration in the cell extracts, which is measured using BCA protein assay kit (Pierce, Rockford, Ill.).

Figure 6:
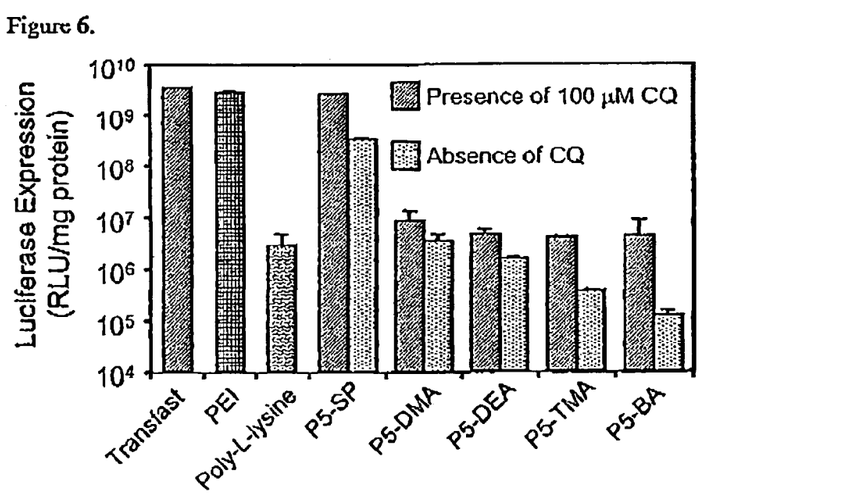
FIG. 6. In vitro transfection efficiency of PPA-DNA coacervates in HEK 293 cells.

FIG. 6 shows the transfection efficiency of PPA-DNA coacervates prepared from five different PPAs with 100 µg/ml of CQ or without CQ, comparing with PEI, PLL and Transfast as gene carriers. Coacervates prepared with P5-SP in the presence of CQ result in the highest transfection efficiency, similar to the level obtained by Transfast-DNA complexes and PEI-DNA complexes. Other PPAs only show moderate transfection activity. It is also evident that CQ can enhance the transfection efficiency for about 4 times at a concentration of 40 µg/ml of CQ, transfection efficiency increases with dose and peaks at a dose of 80 µg/ml of CQ (data not shown). The following experiments are performed with 100 µg/ml of CQ incorporated in the coacervates.

Figure 7:
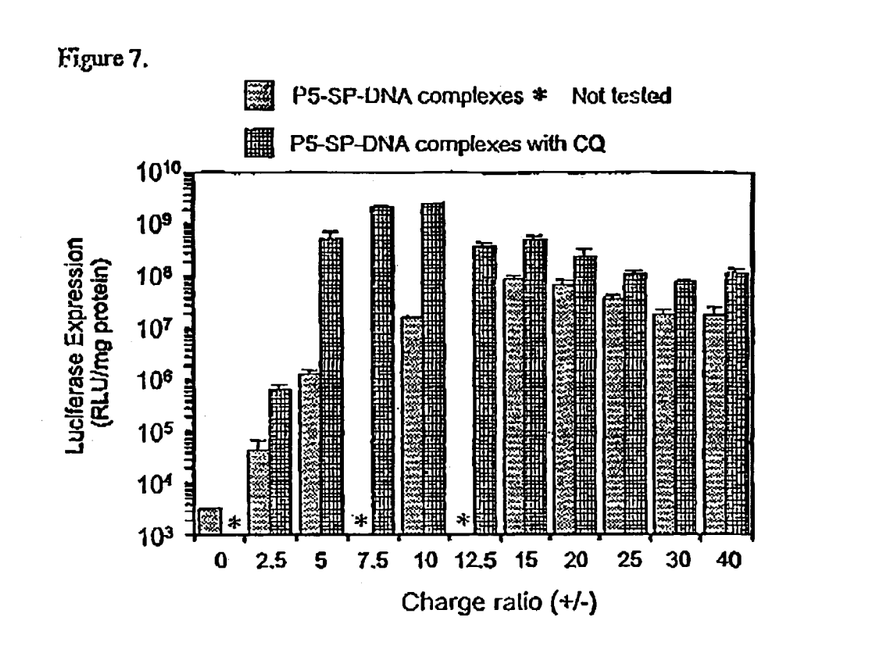
FIG. 7. In vitro transfection efficiency of P5-SP-DNA coacervates in HEK 293 cells at different charge ratios (+/−)

As the gel electrophoresis analysis shows, at a +/− charge ratio of 1.0 (P5-DMA, P5-DEA and P5-TMA) or 1.5 (P5-BA) or 2.0 (P5-SP) and above, all the plasmid DNA added to the preparation mixture is complexed with PPAs. Coacervates prepared at different charge ratios are also examined for their abilities to transfect HEK293 cells (FIG. 7). Although complete DNA incorporation occurs at charge ratio of 2.0 and above for P5-SP, the highest level of gene transfection is observed when the coacervates are synthesized at the +/− charge ratios between 7.5 and above, Transfection efficiency slightly decreases when the charge ratio is 12.5 and above.

Figure 8:
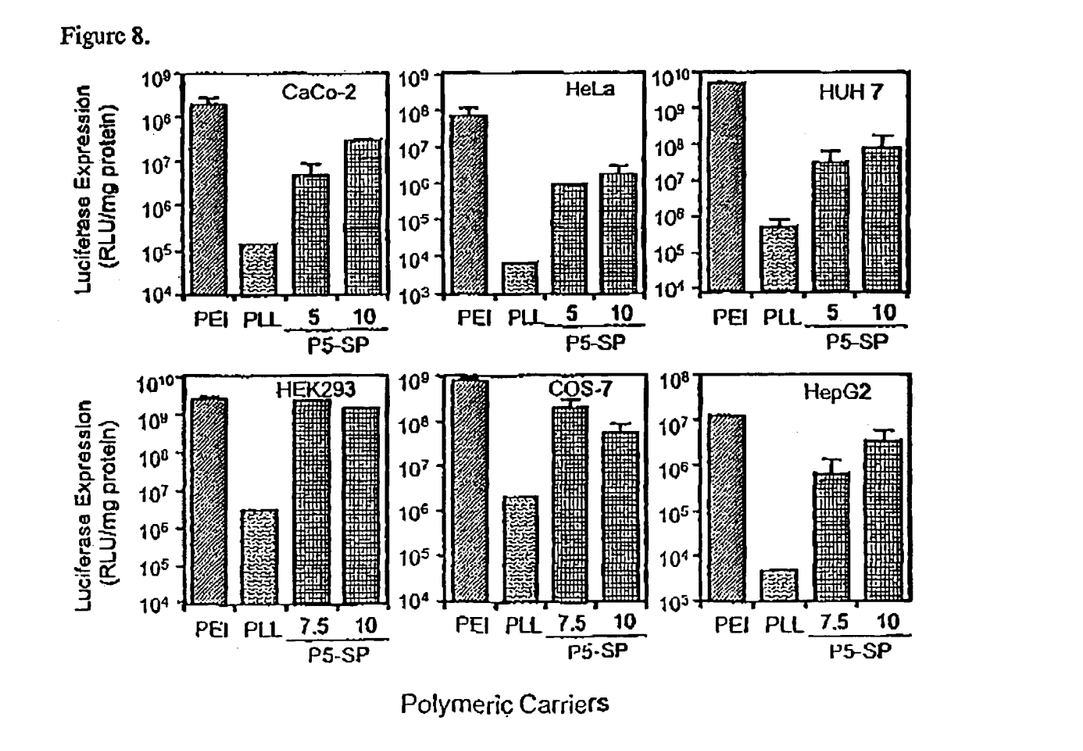
FIG. 8. Transfection of several cell lines using different polymeric carriers and PRE-Luciferase as a model plasmid. P5-SP-DNA coacervates are tested with different charge ratios (5 and 10 for CaCo-2 cells, HeLa cells and HUH 7 cells; 7.5 and 10 for HEK293 cells, COS-7 cells and HepG2 cells)

The transfection efficiency is measured against five other cell lines using PPA-DNA coacervates containing pRE-Luciferase plasmid (FIG. 8). Like in HEK293 cells, the highest level of luciferase expression in CaCo-2 cells, HeLa cells, IIuH-7 cells, COS-7 cells and HepG2 cells is also found to be at a +/− ratio between 5 and 10. The transfection efficiency in CaCO-2 cells, HeLa cells or HuH 7 cells is about 100 to 200 times higher than PLL mediated transfection, and 10 to 50 times lower than that obtained with PHI-DNA complexes. Transfection efficiency in COS-7 cells or HepG2 cells is about 100 to 300 times higher than PLL mediated transfection and 2 folds lower than that obtained with PEI-DNA complexes.

Example 6

Gene Transfection Mediated by PPA Mixtures

Complexes comprising plasmid DNA and PPA mixture were prepared according to a similar procedure as described in Example 4, except that PPA-SP and PPA-DMA were premixed at different ratios before complexation with plasmid DNA. DNA-polymer complexes were formed by adding 50 μl of polymer solution containing varying amounts of polymer to 50 μl of vortexing pRE-luciferase (60 μg/ml, in 0.9% NaCl, pH 7.4) and vortexed for 15-30 s. Complexes were allowed to form for 30 min at room temperature. The complexes were used for transfection study without further purification.

Figure 9:
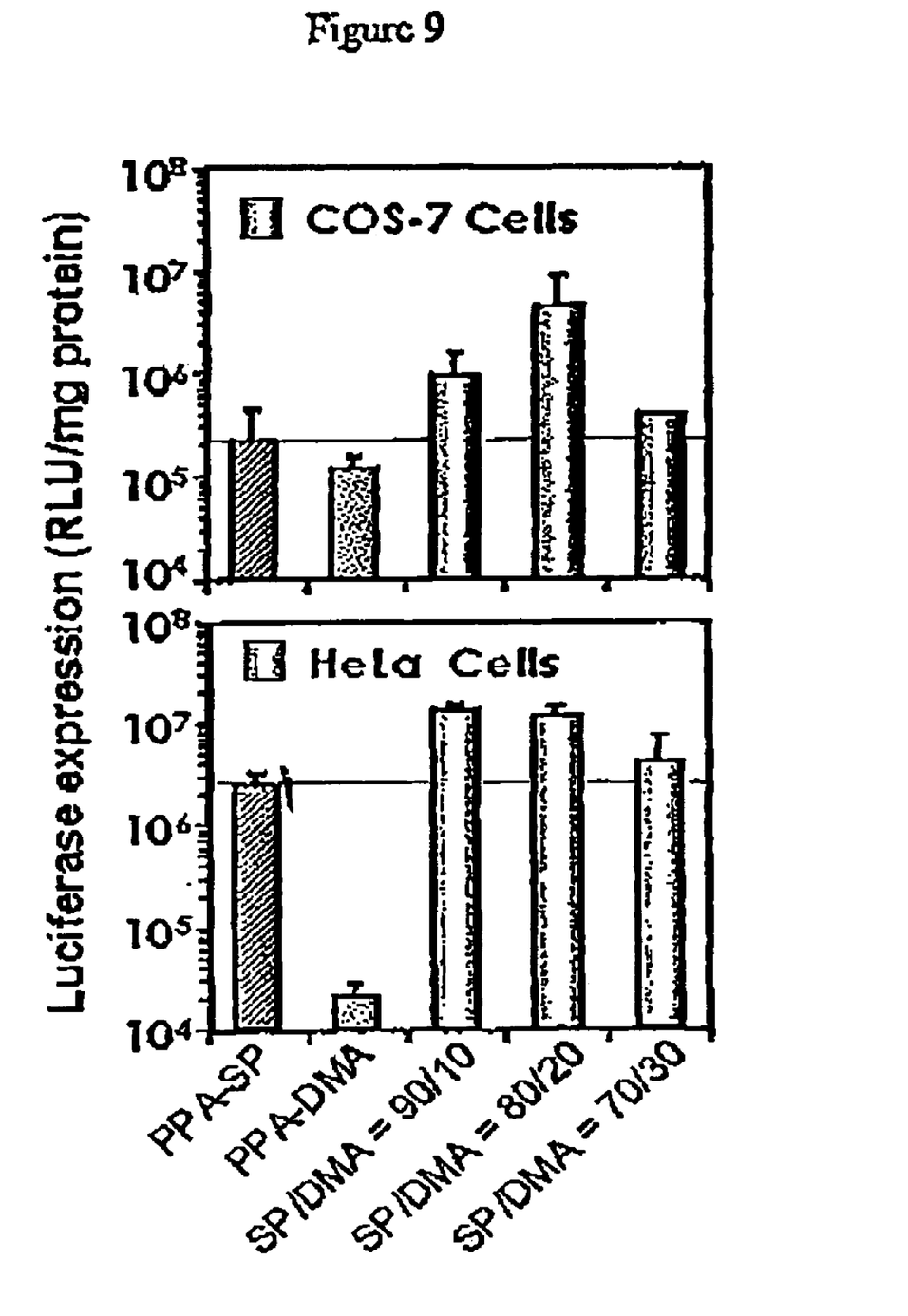
FIG. 9. Transfection mediated by PPA-SP/PPA-DMA mixtures at different molar ratios in COS-7 cells and HeLa cells compared with PPA-SP and PPA-DMA alone.

This is based on the hypothesis that complexes containing various types of amino groups would increase the buffering capacity, thus improve the intracellular delivery of the DNA to cytosol and nucleus. Transfection of COS-7 cells using PPA-SP (containing primary amino group), PPA-DMA (containing tertiary amino group) or PPA-SP/PPA-DMA mixture showed that PPA-SP/PPA-DMA mixture mediated significantly higher levels of gene expression than either polymer alone (FIG. 9, structures see FIG. 3). Transfection was performed with 3 μg DNA per well. The charge ratio of total positive charges in PPA to negative charges in DNA was maintained at 9. Under optimal condition (at a PPA-SP/PPA-DMA molar ratio of 4 to 9), transfection efficiency achieved by PPA-SP/PPA-DMA mixture was 20 and 160 times higher than PPA-SP and PPA-DMA mediated transfection, respectively.

This method of introducing polymeric carriers with different charged groups into the same complexes represents a simple yet effective approach in developing polymeric gene carriers and understanding the mechanisms of polymer mediated gene transfer.

What is claimed is:

1. A water soluble and positively charged biodegradable polyphosphoramidate that is capable of forming a complex with negatively charged bioactive macromolecules in aqueous solutions and comprises the recurring monomeric unit shown in Formula I:

FORMULA I wherein
$R_1$ is a divalent aliphatic organic moiety;
$R_2$ and $R_3$ are each independently selected from the group consisting of hydrogen, alkyl, aryl heteroaryl, heteroalicyclic, cycloalkyl, aralkyl, and cycloalkylalkyl groups;
each non-hydrogen occurrence of $R_2$ and $R_3$ is substituted with one or more positively charged groups; and
n is from 20 to 2,000;

wherein when $R_1$ is $-(CH_2)_a-$ and one of $R_2$ and $R_3$ is hydrogen, the other of $R_3$ and $R_2$ is selected from the group consisting of hydrogen, aryl, heteroaryl, heteroalicylcic, cycloalkyl, aralkyl, and cycloalkylaklyl,
wherein a ranges from 2 to 6.

2. A positively charged biodegradable polyphosphoramidate of claim 1, wherein the biodegradable polyphosphoramidate has between about 20 and about 2,000 phosphoramidate groups.

3. A positively charged biodegradable polyphosphoramidate of claim 2, wherein one or more of $R_1$, $R_2$, or $R_3$ is substituted with one or more groups capable of facilitating intracellular delivery of a negatively charged bioactive macromolecules, selected from the group consisting of lysosomalytic agent, an amphiphilic peptide, and a steroid derivative.

4. A positively charged biodegradable polyphosphoramidate of claim 3, wherein the group capable of facilitating intracellular delivery of negatively charged bioactive macromolecules is a cholesteryl group.

5. A positively charged biodegradable polyphosphoramidate of claim 1, wherein $R_1$ is defined in Formula II:

FORMULA II wherein each occurrence of $R_4$ and $R_5$ are independently selected from the group consisting of hydrogen and alkyl groups; and
q is 2 to 4.

6. A composition comprising a water soluble and positively charged biodegradable polyphosphoramidate that is capable of forming a complex with negatively charged bioactive macromolecules in aqueous solutions having a recurring monomeric unit shown in Formula III:

FORMULA III wherein
$R_1$ is a divalent aliphatic organic moiety;
$R_2$ and $R_3$ are each independently selected from the group consisting of hydrogen, alkyl, aryl, heteroaryl, heteroalicyclic, cycloalkyl, aralkyl, and cycloalkylalkyl groups;
each non-hydrogen occurrence of $R_2$ and $R_3$ is substituted with one or more positively charged groups;
$R_4$ and $R_5$ are independently selected from the group consisting of alkyl, cycloalkyl, alkoxy, aryl, heteroaryl, heteroalicycic, aralkyl, and a steroid derivative;
q is from about 1 to about 5; and
n is from about 20 to about 2,000.

7. The composition of claim 1, wherein the biodegradable polyphosphoramidate has between about 20 and about 2,000 phosphoramidate groups.

8. The composition of claim 1, wherein non-hydrogen occurrences $R_2$ and $R_3$ are substituted with one or more charged groups selected from the group consisting of primary amine, secondary amine, tertiary amine, quaternary amine, and imidazoyl.

9. The composition of claim 2, wherein one or more of $R_1$, $R_2$, or $R_3$ is substituted with one or more groups capable of facilitating intracellular delivery of a negatively charged bioactive macromolecules, selected from the group consisting of lysosomalytic agent, an amphiphiic peptide, and a steroid derivative.

10. The composition of claim 3, wherein the group capable of facilitating intracellular delivery of negatively charged bioactive macromolecules is a cholesterol group.

11. The positively charged biodegradable polyphosphoramidate of claim 1, wherein non-hydrogen occurrences $R_2$ and $R_3$ are substituted with one or more charged groups selected from the group consisting of primary amine, secondary amine, tertiary amine, quaternary amine and imidazoyl.

\* \* \* \* \*